United States Patent [19]

Sayo et al.

[11] Patent Number: 4,766,225
[45] Date of Patent: Aug. 23, 1988

[54] RUTHENIUM-PHOSPHINE COMPLEX

[75] Inventors: Noboru Sayo, Kanagawa; Takanao Taketomi, Chiba; Hidenori Kumobayashi; Susumu Akutagawa, both of Kanagawa, all of Japan

[73] Assignee: Takasago International Corporation, Tokyo, Japan

[21] Appl. No.: 130,577

[22] Filed: Dec. 9, 1987

[30] Foreign Application Priority Data

Dec. 9, 1986 [JP] Japan .................................. 61-293075

[51] Int. Cl.$^4$ ............................................. C07F 15/00
[52] U.S. Cl. ......................................................... 556/16
[58] Field of Search ............................................ 556/16

[56] References Cited

U.S. PATENT DOCUMENTS 4,604,474  8/1986  Kumobayashi et al. ......... 556/16 X
4,691,037  9/1987  Yoshikawa et al. .............. 556/16 X

*Primary Examiner*—Paul F. Shaver
*Attorney, Agent, or Firm*—Sughrue, Mion, Zinn, Macpeak, and Seas

[57] ABSTRACT

A ruthenium-phosphine complex represented by formula (I):

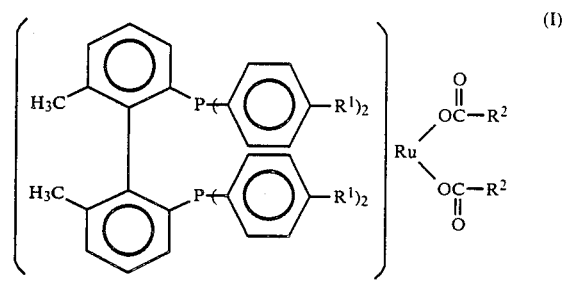

wherein $R^1$ represents a hydrogen atom, a methyl group, or a methoxy group; and $R^2$ represents a lower alkyl group, a halogenated lower alkyl group, a phenyl group, or a phenyl group substituted with a lower alkyl group. The complex is inexpensive and exhibits excellent performance as a catalyst for various organic syntheses, particularly for asymmetric hydrogenation.

5 Claims, No Drawings

RUTHENIUM-PHOSPHINE COMPLEX

FIELD OF THE INVENTION

This invention relates to a ruthenium-phosphine complex useful as a catalyst for various organic syntheses, particularly for asymmetric hydrogenation reaction, and the like.

BACKGROUND OF THE INVENTION

Various organic synthetic reactions using metal complexes have hitherto been developed and utilized for many purposes. In particular, there are a number of reports on asymmetric catalysts to be used in asymmetric synthesis, i.e., asymmetric isomerization, asymmetric hydrogenation, and the like. Of the reported asymmetric catalysts, metal complexes formed between metallic rhodium and an optically active tertiary phosphine are especially well known as catalysts for asymmetric hydrogenation. Such complexes typically include a rhodium-phosphine complex using 2,2'-bis(diphenylphosphino)-1,1'-binaphthyl (hereinafter abbreviated as BINAP) as a ligand as disclosed in Japanese Patent Application (OPI) No. 61937/80 (the term "OPI" as used herein means an "unexamined published Japanese patent application").

Inoue et al reports in *Chemistry Letters*, p. 1007–1008 (1985) that they obtained citronellol by asymmetric hydrogenation of geraniol or nerol using various rhodium-phosphine catalysts in an optical yield of 66%.

Other examples of the ligand include a rhodium-phosphine complex using 2,2'-bis(diphenylphosphino)-6,6'-dimethylbiphenyl as disclosed in Japanese Patent Application (OPI) No. 65051/84.

On the other hand, known ruthenium complexes, though there are not so many reports as compared with rhodium complexes, include those having BINAP or 2,2'-bis(di-p-tolylphosphino)-1,1'-binaphthyl (hereinafter abbreviated as T-BINAP) as a ligand, e.g., $Ru_2Cl_4$(BINAP)$_2$(NEt$_3$) (wherein Et represents an ethyl group, hereinafter the same), $Ru_2Cl_4$(T-BINAP)$_2$(NEt$_3$), RuHCl(BINAP)$_2$, and RuHCl(T-BINAP)$_2$, as reported in Ikariya et al., *J. Chem. Soc., Chem. Commun.*, p. 922, (1985). However, the state-of-the-art ruthenium complexes are not satisfactory in stability as well as optical yield attained.

Although metallic rhodium provides excellent complex catalysts, it is expensive due to limitations in place and quantity of production. When used as a catalyst component, it forms a large proportion in cost of the catalyst, ultimately resulting in increase in cost of the final commercial products. While metallic ruthenium is cheaper than rhodium and appears promising as a catalyst component for industrial application, it still has problems in its activity to cope with precision reactions and its range of application. Therefore, it has been keenly demanded to develop a catalyst which is inexpensive, has high activity and durability, and catalyzes asymmetric reactions to attain high optical yields, i.e., to produce reaction products having high optical purity.

SUMMARY OF THE INVENTION

As a result of extensive investigations with the purpose of meeting the above-described industrial demand, the inventors have discovered a novel ruthenium complex having high catalytic activity, which is usable either for general syntheses when the ligand thereof is optically inactive or for asymmetric syntheses when the ligand thereof is optically active. The present invention has been completed based on this finding.

The present invention relates to a ruthenium-phosphine complex represented by formula (I)

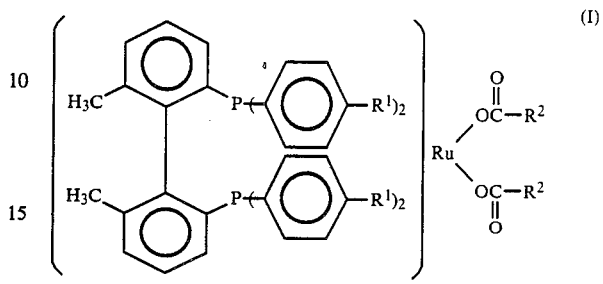

wherein $R^1$ represents a hydrogen atom, a methyl group, or a methoxy group; and $R^2$ represents a lower alkyl group, a halogenated lower alkyl group, a phenyl group, or a phenyl group substituted with a lower alkyl group.

DETAILED DESCRIPTION OF THE INVENTION

In the definition for formula (I) as described above, the lower alkyl group preferably contains from 1 to 4 carbon atoms; and examples of the halogen in the halogenated lower alkyl group include flourine, chorine, and bromine.

The 2,2'-bis(diarylphosphino)-6,6'-dimethylbiphenyl as a ligand of the complex of the present invention can be synthesized according to the process reported in Miyashita et al., *The Chemical Society of Japan, Collected Drafts II for Lectures in the 52th spring Annual Meeting*, IT06, p. 1267 (1986). More specifically, o-toluidine is reacted with nitric acid to form 2-amino-3-methylnitrobenzene, which is then converted to 2-iodo-3-methylnitrobenzene making use of the process described in P. B. Carlin et al., *J. Am. Chem. Soc.*, Vol. 78, p. 1997 (1956). A copper powder is reacted on the resulting product to obtain 2,2'-dinitro-6,6'-dimethylbiphenyl, which is then subjected to hydrogenation using a Raney nickel as a catalyst to obtain 2,2'-diamino-6,6'-dimethylbiphenyl. The product is treated with a 47% hydrobromic acid aqueous solution to obtain 2,2'-dibromo-6,6'-dimethylbiphenyl. A Grignard reagent is prepared from the product according to a process generally employed therefor, for example, by using magnesium. The resulting Grignard reagent is condensed with a diarylphosphinyl chloride selected from diphenylphosphinyl chloride, di-p-tolylphosphinyl chloride, and di-p-anisylphosphinyl chloride to obtain a (±)-2,2'-bis(diarylphosphino)-6,6'-dimethylbenzyl. The product is resolved by using benzoyl tartrate and then reduced with trichlorosilane to obtain an optically active 2,2'-bis(diarylphosphino)-6,6'-dimethylbiphenyl. Starting with the thus prepared optically active 2,2'-bis(diarylphosphino)-6,6'-dimethylbiphenyl, there can be obtained the ruthenium-phosphine complex of the present invention having the corresponding optical activity.

The ruthenium-phosphine complex of formula (I) according to the present invention can be prepared starting from $Ru_2Cl_4(L)_2NEt_3$ (wherein L represents a 2,2'-bis(diarylphosphino)-6,6'-dimethylbiphenyl, hereinafter the same), which is obtained by reacting [RuCl$_2$-

(COD)]$_n$ (wherein COD represents cyclooctadiene, hereinafter the same) and the above-described 2,2'-bis(diarylphosphino)-6,6'-dimethylbiphenyl.

The starting material, [RuCl$_2$(COD)]$_n$, can be prepared by reacting ruthenium chloride and cycloocta-1,5-diene in an ethanol solvent as taught in M. A. Bennett et al., *Chemistry and Ind.*, p. 1516 (1959). Ru$_2$Cl$_4$(L)$_2$NEt$_3$ can be obtained in a good yield by reacting 1 mole of [RuCl$_2$(COD)]$_n$, about 1.2 moles of 2,2'-bis(diarylphosphino)-6,6'-dimethylbiphenyl, and about 4 moles of triethylamine in a solvent, e.g., toluene, under heating.

The novel ruthenium-phosphine complex of formula (I) according to the present invention can be prepared as follows. Ru$_2$Cl$_4$(L)$_2$NEt$_3$ and a carboxylic acid salt are reacted in an alcohol solvent, e.g., methanol, ethanol, t-butanol, etc., at a temperature of from about 20° to 110° C. for a period of from 3 to 15 hours. The solvent is removed by distillation, and the desired complex is extracted with a solvent, e.g., diethyl ether, ethanol, etc., followed by evaporating to dryness to obtain a crude complex. The resulting crude complex as produced may be used as a catalyst for asymmetric hydrogenation, and the like or, if desired, may be purified by recrystallization from a solvent, e.g., ethyl acetate, etc.

Ruthenium-phosphine complexes having any desired acyloxyl group introduced can be obtained by varying the kind of the carboxylic acid salt used. Specific examples of the carboxylic acid salts which can be used are sodium acetate, sodium propionate, potassium acetate, silver acetate, sodium butyrate, sodium isobutyrate, sodium pivalate, sodium monochloroacetate, sodium dichloroacetate, sodium trichloroacetate, sodium benzoate, sodium p-tolylbenzoate, etc.

For instance, complexes of formula (I) having a trifluoroacetic group are obtained by reacting a diacetate complex, Ru(O$_2$CCH$_3$)$_2$(L), as prepared by the above-described process with trifluoroacetic acid in methylene chloride as a solvent at about 25° C. for about 12 hours.

Specific examples of the ruthenium-phosphine complexes according to the present invention are shown below.

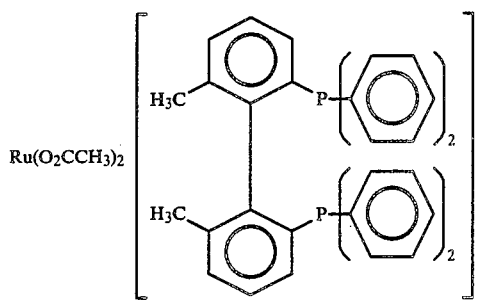
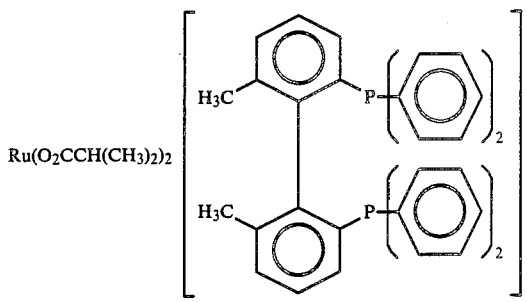
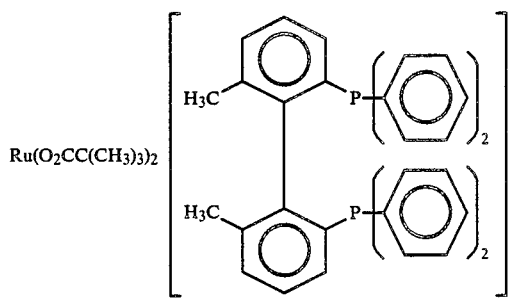
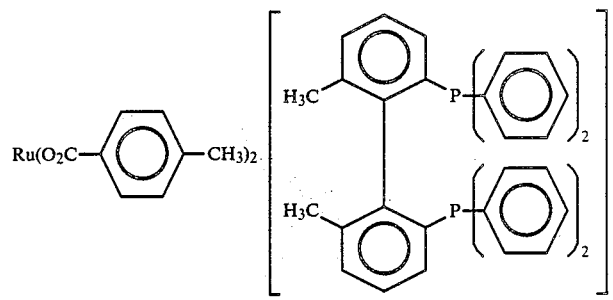
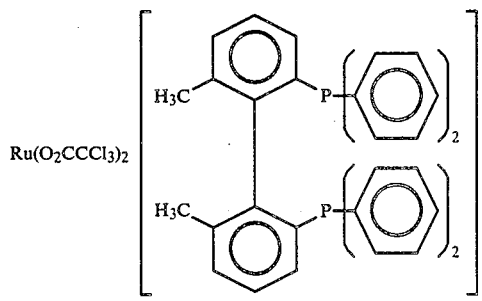
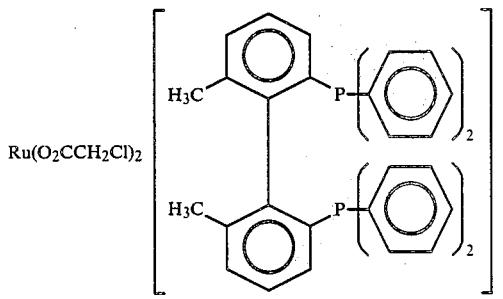

-continued
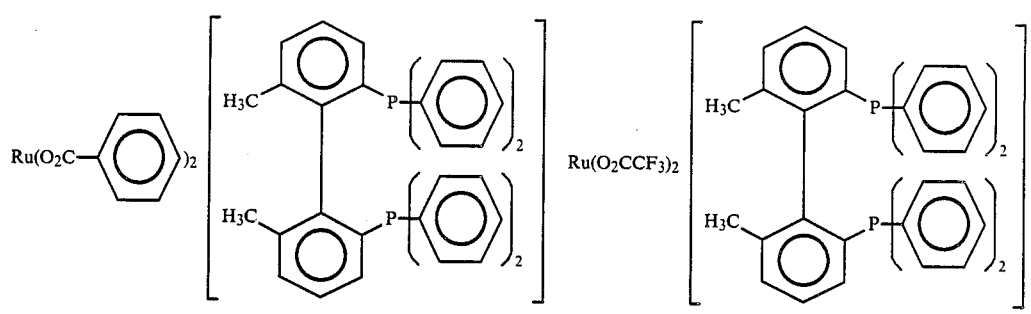
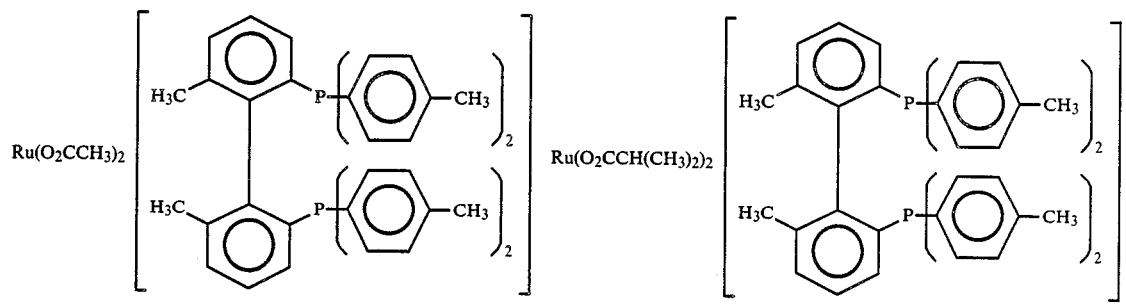
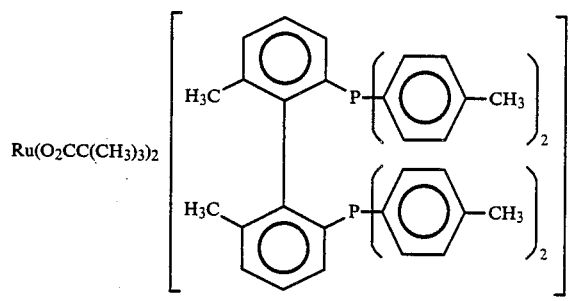
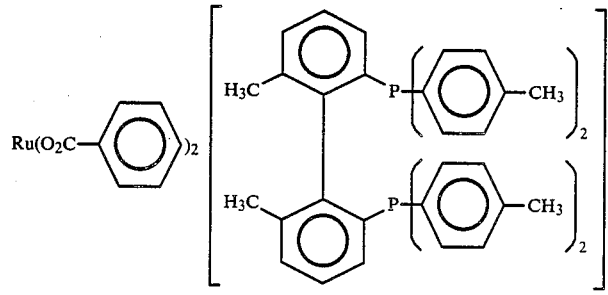
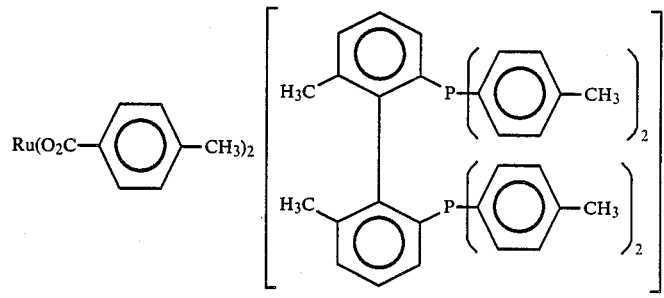

-continued
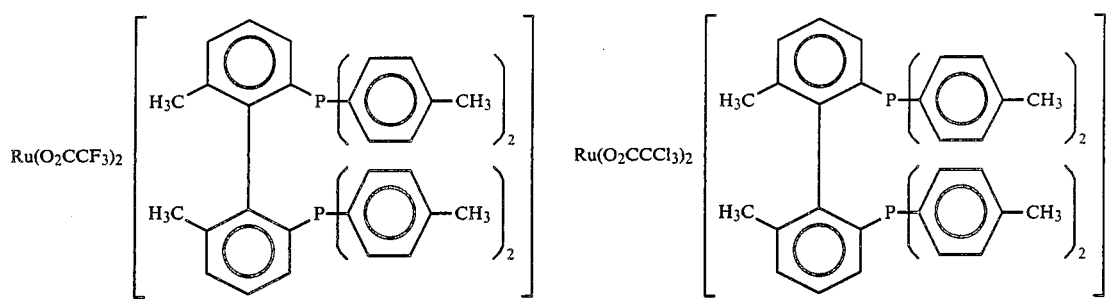
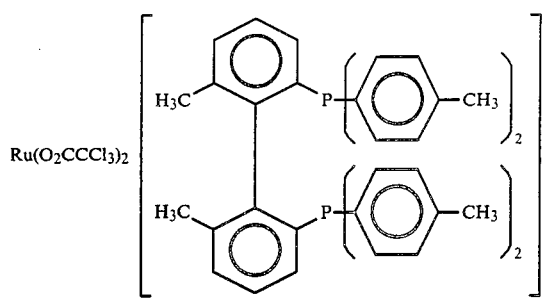
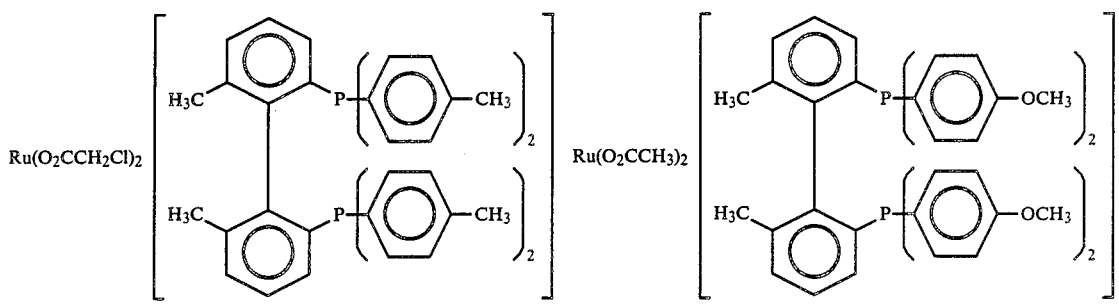
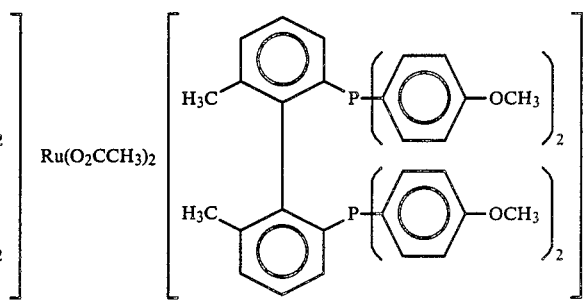
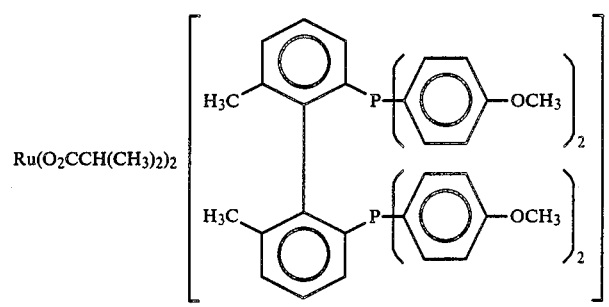
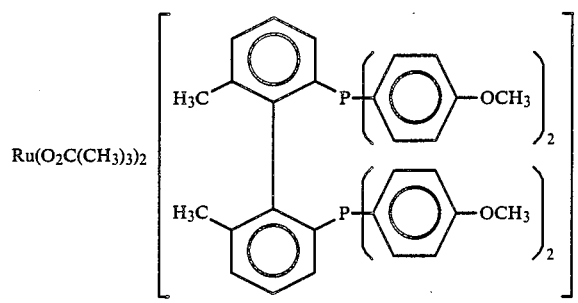
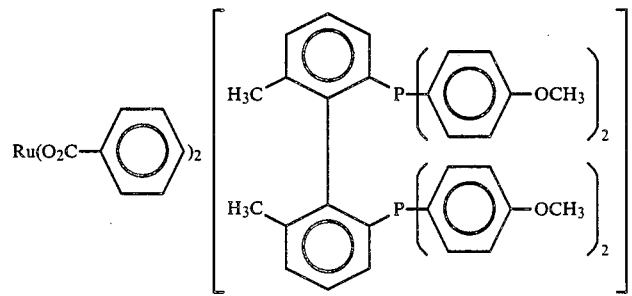

-continued

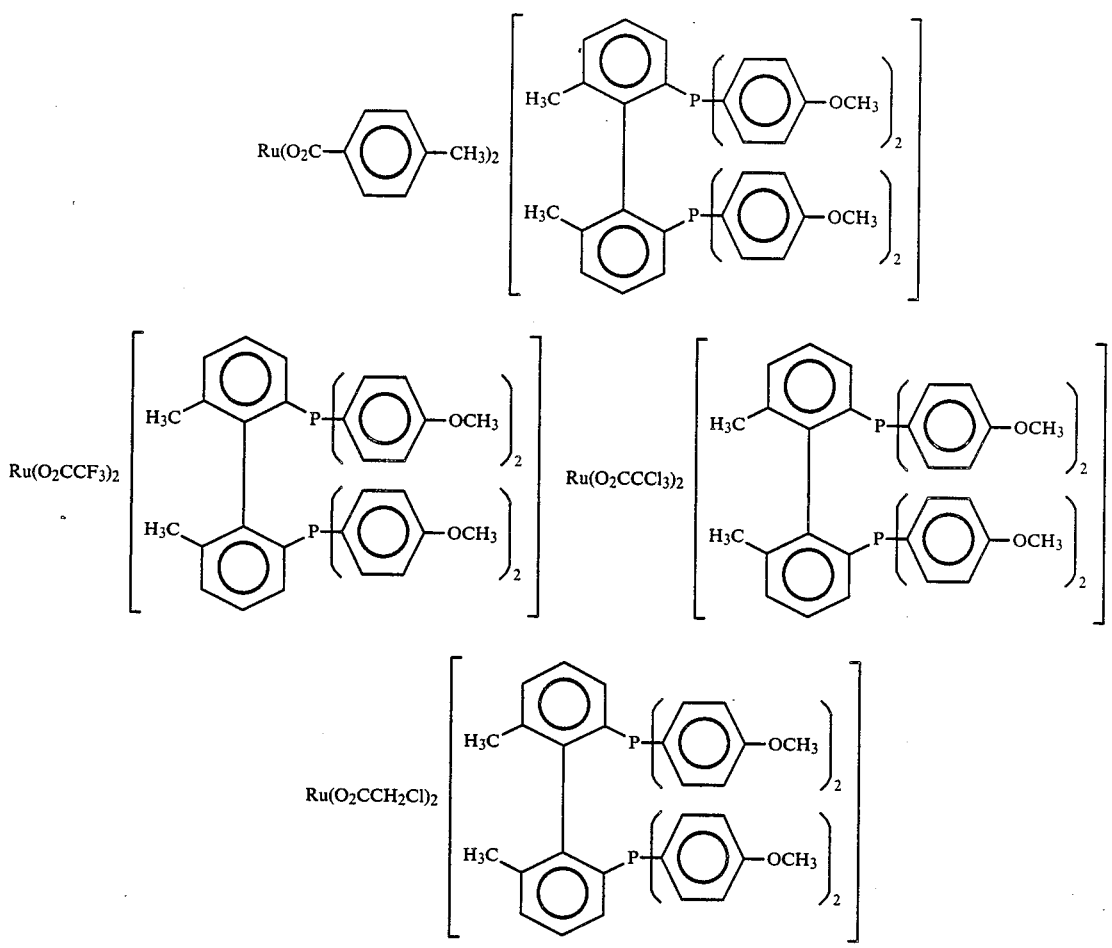

The thus obtained ruthenium-phosphine complex of formula (I) according to the present invention contains a biphenyl basic structure as a ligand that exhibits higher structural flexibility and higher solubilities to various solvents and is, therefore, more applicable to various reactions as compared with a BINAP ligand. The ruthenium-phosphine complex of the invention exhibits excellent performance as a catalyst for asymmetric hydrogenation or the like reaction. For example, when it is applied to asymmetric hydrogenation of α,β-unsaturated carboxylic acids, such as tiglic acid, atropic acid, etc., it exhibits very high catalytic activities event at room temperature. More specifically, the reaction rapidly proceeds in the presence of the complex at a molar concentration of from 1/200 to 1/1000 based on a substrate, e.g., 6-methoxy-α-methylene-2-naphthaleneacetic acid, to produce naproxen, i.e., a hydrogenation product, at a selectivity reaching almost 100%. Further, the thus produced naproxen has an optical purity of from 90 to 95%. Thus, the ruthenium-phosphine complexes according to the present invention show very excellent results as industrially useful catalysts.

The present invention will hereinafter be illustrated in greater detail with reference to Reference Example, Examples, and Use Example, but it should be understood that the present invention is not deemed to be limited thereto.

REFERENCE EXAMPLE

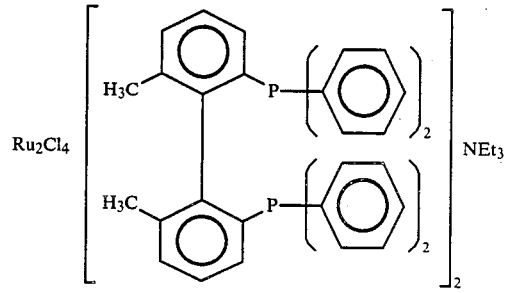

[Bis(μ,μ'-dichloro)bis{2,2'-bis(diphenylphosphino)-6,6'-dimethylbiphenyl}]diruthenium-Triethylamine To 50 ml of toluene were added 0.5 g (1.8 mmoles) of [RuCl$_2$(COD)]$_n$, 1 g (1.82 mmoles) of 2,2'-bis(diphenylphosphino)-6,6'-dimethylbiphenyl, and 1.0 ml (7.2 mmoles) of triethylamine under a nitrogen atmosphere, and the mixture was stirred while heating under toluene refluxing for 6 hours to effect reaction. The solvent was removed from the reaction mixture by distillation, and the residue was dried under reduced pressure. The solid was dissolved in methylene chloride, followed by filtration through Celite. The filtrate was concentrated to dryness under reduced pressure to obtain 1.35 g of the titled compound as deep red crystals. The yield was 97%.

Elemental Analysis for $C_{82}H_{79}P_4NCl_4Ru_2$: Calcd. (%): Ru 13.07, P 8.01, C 63.69, H 5.15. Found (%): Ru 12.71, P 7.64, C 64.07, H 5.52.

$^{31}P$ NMR (CDCl$_3$) δ ppm: 51.63 (d, J=40.0 Hz), 52.52 (d, J=41.5 Hz)

$^1H$ NMR (CDCl$_3$) δ ppm: 1.27 (s, 12H), 1.30 br. s, 9H), 2.91–3.08 (m, 6H), 6.58–8.18 (m, 52H)

EXAMPLE 1

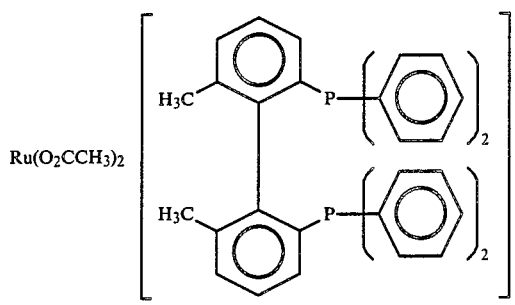

[2,2'-Bis(diphenylphosphino)-6,6'-dimethylbiphenyl]ruthenium-Diacetate

In a 80 ml-volume Schlenk's tube were charged 0.66 g (0.85 mmole) of the [bis(μ,μ'-dichloro)bis{2,2'-bis(diphenylphosphino)-6,6'-dimethylbiphenyl}]diruthenium-triethylamine as prepared in Reference Example and 0.70 g (8.54 mmoles) of sodium acetate. After the atmosphere had been thoroughly displaced with nitrogen, 40 ml of t-butanol was added thereto, followed by heat-refluxing for 14 hours. After completion of the reaction, the t-butanol was removed by distillation under reduced pressure, and the residue was evaporated to dryness and extracted three times with 5 ml portions of diethyl ether. The diethyl ether was removed by distillation to dryness, and the solid was further extracted three times with 5 ml portions of ethanol. The extract was concentrated to dryness to obtain 0.65 g of the titled compound as a yellowish brown solid. The yield was 98.6%.

Elemental Analysis for $C_{42}H_{44}O_4P_2Ru$: Calcd. (%): Ru 13.03; P 7.98; C 65.02; H 5.72. Found (%): Ru 12.69; P 7.78; C 65.41; H 6.08.

$^{31}P$ NMR (CDCl$_3$) δ ppm: 61.18 (s)

$^1H$ NMR (CDCl$_3$) δ ppm: 1.32 (s, 6H), 1.72 (s, 6H), 6.61–7.72 (m, 26H)

EXAMPLE 2

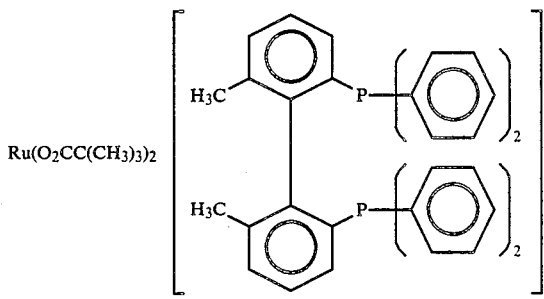

[2,2'-Bis(diphenylphosphino)-6,6'-dimethylbiphenyl]ruthenium-Dipivalate

In a 80 ml-volume Schlenk's tube were charged 0.39 g (0.5 mmole) of the [bis(μ,μ'-dichloro)bis{2,2'-bis(diphenylphosphino)-6,6'-dimethylbiphenyl}]diruthenium-triethylamine as prepared in Reference Example and 0.62 g (5 mmoles) of sodium pivalate. After the atmosphere had been thoroughly displaced with nitrogen, 30 ml of t-butanol was added thereto, followed by heat-refluxing for 12 hours. After completion of the reaction, the t-butanol was removed by distillation under reduced pressure, and the residue was evaporated to dryness and extracted three times with 5 ml portions of diethyl ether. The extract was concentrated to dryness to obtain 0.42 g of the titled compound as a yellowish brown solid. The yield was 98%.

Elemental Analysis for $C_{48}H_{50}O_4P_2Ru$: Calcd. (%): Ru 11.84; P 7.25; C 67.51; H 5.90. Found (%): Ru 11.55; P 6.91; C 67.91; H 6.31.

$^{31}P$ NMR (CDCl$_3$) δ ppm: 65.71 (s)

$^1H$ NMR (CDCl$_3$) δ ppm: 0.90 (s, 18H), 1.35 (s, 6H), 6.58–7.68 (m, 26H)

EXAMPLE 3

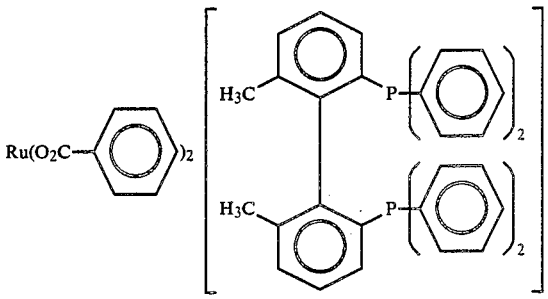

[2,2'-Bis(diphenylphosphino)-6,6'-dimethylbiphenyl]ruthenium-Dibenzoate

In a 80 ml-volume Schlenk's tube were charged 0.39 g (0.5 mmole) of the [bis(μ,μ'-dichloro)bis{2,2'-bis(diphenylphosphino)-6,6'-dimethylbiphenyl}]diruthenium-triethylamine as prepared in Reference Example and 0.72 g (5.0 mmoles) of sodium benzoate. After the atmosphere had been thoroughly displaced with nitrogen, 30 ml of t-butanol was added thereto, followed by heat-refluxing for 12 hours. After completion of the reaction, the t-butanol was removed by distillation under reduced pressure, and the residue was evaporated to dryness and extracted three times with 5 ml portions of diethyl ether. The diethyl ether was removed by distillation to dryness, and the solid was further extracted three times with 5 ml portions of ethanol. The extract was concentrated to dryness to obtain 4.4 g of the titled compound as a yellowish brown solid. The yield was 98%.

Elemental Analysis for $C_{52}H_{42}O_4P_2Ru$: Calcd. (%): Ru 11.31; P 6.90; C 69.89; H 4.72. Found (%): Ru 10.97; P 6.63; C 70.12; H 5.08.

$^{31}P$ NMR (CDCl$_3$) δ ppm: 65.78 (s)

$^1H$ NMR (CDCl$_3$) δ ppm: 1.30 (s, 6H), 6.65–7.80 (m, 36H)

EXAMPLE 4

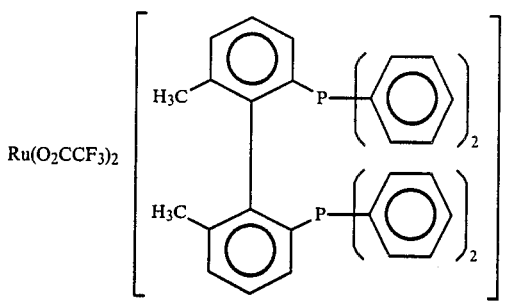

[2,2'-Bis(diphenylphosphino)-6,6'-dimethylbiphenyl]ruthenium-Ditrifluroacetate

In a Schlenk's tube whose atmosphere had been replaced with nitrogen, 0.39 g (0.5 mmole) of the [2,2'-bis(diphenylphosphino)-6,6'-dimethylbiphenyl]ruthenium-diacetate as prepared in Example 1 was charged, and 5 ml of methylene chloride was added thereto to form a uniform solution. To the solution was added 0.09 ml (1.15 mmoles) of trifluoroacetic acid which had been purified by distillation, followed by stirring at room temperature for 12 hours. After completion of the reaction, the reaction mixture was concentrated to dryness to obtain 0.44 g of a crude complex. The resulting complex was dissolved in methylene chloride, and the solution was filtered through Celite. The filtrate was concentrated to dryness to obtain 0.42 g of the titled compound as a deep brown solid. The yield was 96%.

Elemental Analysis for $C_{42}H_{32}O_4F_6P_2Ru$: Calcd. (%): Ru 11.52; P 7.06; C 57.47; H 3.67. Found (%): Ru 11.18; P 6.76; C 57.81; H 3.91.

$^{31}P$ NMR $(CDCl_3)$ δ ppm: 61.87 (s)

$^1H$ NMR $(CDCl_3)$ δ ppm: 1.27 (s, 6H), 6.10–7.21 (m, 6H)

USE EXAMPLE

In a 200 ml-volume autoclave were charged 15.4 mg (0.02 moles) of the [2,2'-bis(diphenylphosphino)-6,6'-dimethylbiphenyl]ruthenium-diacetate as prepared in Example 1, 2.45 g (5 mmoles) of 6-methoxy-α-methylene-2-naphthaleneacetic acid, 0.98 g (5 mmoles) of dicyclohexylmethylamine, and 50 ml of ethanol. The mixture was subjected to hydrogenation at 15° C. under a hydrogen pressure of 100 kg/cm² for 12 hours, and the solvent was removed from the reaction mixture by distillation to obtain 2.40 g of naproxen (i.e., 6-methoxy-α-methyl-2-naphthaleneacetic acid). The yield was 97%.

Melting Point: 154°–155° C.

Optical Rotation: $[\alpha]_D^{25}$ +59.60° (c=1.0, $CHCl_3$)

$^1H$ NMR δ ppm: 1.57 (d, 3H), 3.86 (q, 1H), 3.90 (s, 3H), 7.07–7.87 (m, 6H), 10.83 (s, 1H)

The resulting carboxylic acid was reacted with (R)-(+)-1-(1-naphthyl)ethylamine to synthesize an amide compound. High performance liquid chromatography of the amide revealed that the above obtained carboxylic acid comprised 95.5% of (S)-naproxen having an optical purity of 91.0%ee and 4.5% of (R)-naproxen.

The present invention provides a novel ruthenium-phosphine complex exhibiting excellent performance as a catalyst for various organic syntheses, and particularly asymmetric hydrogenation, and shows industrially superior results in selective hydrogenation of olefins as well as in catalytic activity. Further, the complex according to the present invention can be produced at low cost, making a contribution to reduction of product price and, thus, has a high industrial value.

While the invention has been described in detail and with reference to specific embodiments thereof, it will be apparent to one skilled in the art that various changes and modifications can be made therein without departing from the spirit and scope thereof.

What is claimed is:

1. A ruthenium-phosphine complex represented by formula (I):

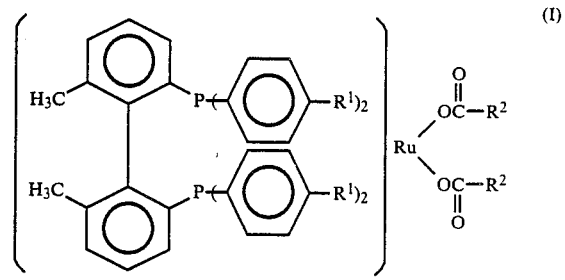

wherein $R^1$ represents a hydrogen atom, a methyl group, or a methoxy group; and $R^2$ represents a lower alkyl group, a halogenated lower alkyl group, a phenyl group, or a phenyl group substituted with a lower alkyl group.

2. [2,2'-Bis(diphenylphosphino)-6,6'-dimethylbiphenyl]ruthenium-diacetate, according to claim 1.

3. [2,2'-Bis(diphenylphosphino)-6,6'-dimethylbiphenyl]ruthenium-dipivalate, according to claim 1.

4. [2,2'-Bis(diphenylphosphino)-6,6'-dimethylbiphenyl]ruthenium-dibenzoate, according to claim 1.

5. [2,2'-Bis(diphenylphosphino)-6,6'-dimethylbiphenyl]ruthenium-ditrifluoroacetate, according to claim 1.

* * * * *